United States Patent [19]

Sawicki

[11] 4,367,347
[45] Jan. 4, 1983

[54] HIGH PURITY 2,4-DINITROTOLUENE FROM TOLUENE NITRATION PROCESS

[75] Inventor: John E. Sawicki, Breinigsville, Pa.

[73] Assignee: Air Products and Chemicals, Inc., Allentown, Pa.

[21] Appl. No.: 269,137

[22] Filed: Jun. 1, 1981

[51] Int. Cl.³ .............................................. C07C 79/10
[52] U.S. Cl. .................................................. 568/934
[58] Field of Search ............................... 568/934, 935

[56] References Cited

U.S. PATENT DOCUMENTS

| | | | |
|---|---|---|---|
| 2,362,743 | 2/1943 | Crater | 568/934 |
| 2,765,348 | 10/1956 | Baumgartner et al. | 568/934 |
| 3,178,481 | 1/1963 | Hauze | 568/934 |
| 3,243,466 | 3/1966 | Brogden et al. | 568/934 |
| 3,708,546 | 1/1973 | Coon et al. | 568/934 |
| 3,799,993 | 3/1974 | Hill et al. | 568/934 |
| 3,931,347 | 1/1976 | Rosenblatt et al. | 568/934 |

FOREIGN PATENT DOCUMENTS 263018 12/1926 United Kingdom ................ 568/934

*Primary Examiner*—Leland A. Sebastian
*Attorney, Agent, or Firm*—Michael Leach; E. Eugene Innis; James C. Simmons

[57] ABSTRACT

A method for preparing substantially pure 2,4-DNT isomer from its admixture with other DNT isomers which comprises contacting the isomer mixture with aqueous sulfuric acid at an elevated temperature, separating excess DNT isomer mixture from the sulfuric acid phase and cooling the sulfuric acid phase. Also, in a method for producing dinitrotoluenes which comprises:

(a) nitrating toluene in a first nitration stage with an aqueous mixture of sulfuric and nitric acids to form an organic phase containing mononitrotoluenes and a first aqueous spent acid phase;

(b) separating the organic phase from the first aqueous spent acid phase;

(c) nitrating the mononitrotoluenes contained in the organic phase in a second nitration stage using a mixture of sulfuric and nitric acids to form an organic phase containing dinitrotoluenes and a second aqueous spent acid phase; and (d) separating the organic phase from the second aqueous spent acid phase for recovery of the dinitrotoluene product from the organic phase;

the novel feature comprising:

(e) cooling at least a portion of the first or second aqueous spent acid phase to a temperature sufficient to effect crystallization of substantially pure 2,4-DNT;

(f) recovering the 2,4-DNT crystals from the cooled aqueous spent acid phase; and (g) returning the portion of the cooled spent acid phase to a nitration stage.

20 Claims, 3 Drawing Figures

HIGH PURITY 2,4-DINITROTOLUENE FROM TOLUENE NITRATION PROCESS

TECHNICAL FIELD

This invention relates to a method for recovering 2,4-dinitrotoluene. More specifically, the present invention relates to a method for isolating substantially pure 2,4-dinitrotoluene from a mixture of dinitrotoluene isomers.

BACKGROUND OF THE INVENTION

Nitroaromatics, particularly dinitrotoluenes (DNT), are widely used as intermediates in the manufacture of aromatic amines, for example toluenediamine, which then can be converted to isocyanates for polyurethane manufacture. Commercially, dinitrotoluenes are typically produced by the mixed acid nitration of toluene, the mixed acid being a mixture of concentrated sulfuric acid and nitric acid. In this process mononitrotoluene is formed in a first nitration stage and then separated from the aqueous phase. The crude mononitrotoluenes are then nitrated with fresh nitrating acid in a second nitration stage. The DNT product is then separated from the aqueous phase for recovery with the aqueous phase being recycled to a nitration stage.

Other methods for producing DNT are taught in U.S. Pat. Nos. 2,362,743; 3,178,481; 3,243,466; and 3,708,546.

U.S. Pat. No. 2,362,743 describes a process for the manufacture of DNT and particularly 2,4-DNT by a two stage nitration process in which no sulfuric acid is used.

U.S. Pat. No. 3,178,481 discloses a method for producing a DNT product having a high percentage of the 2,4-DNT isomer using a loop reaction scheme which makes DNT from toluene in one nitration stage.

U.S. Pat. No. 3,243,466 describes a continuous process for the manufacture of DNT from toluene in a series of four nitration vessels.

U.S. Pat. No. 3,708,546 discloses a process for nitrating toluene to a mixture of DNT isomers high in the 2,4-DNT isomer by reacting the toluene with a mixture of nitric and sulfuric acids at sub-zero temperatures in the presence of a small amount of water. The DNT product is recovered from the reaction mixture by solvent extraction with methylene chloride.

Commercially produced DNT is a combination of six isomers. Each of these isomers has a market of its own in specialty chemicals and the more desirable isomers can be sold at a premium price. The problem, however, is to separate and recover the more desirable isomers from the DNT process and, ideally, not adversely change the composition of the product DNT which must meet certain commercial specifications. Because of this problem, standard separation techniques, for example distillation and crystallization, are usually performed on a "product" grade isomer mixture from a DNT process in order to isolate a particular DNT isomer.

One such separation technique is taught in U.S. Pat. No. 2,765,348 which discloses a process for obtaining 2,6-DNT from its admixture with 2,4-DNT and other impurities. Aniline or a lower alkyl substituted aniline is added to an isomer mixture of 2,4-DNT; 2,6-DNT and impurities. The resulting mixture is cooled below 0° C. but above the temperature at which the mass solidifies. The crystals of 2,6-DNT which form are then recovered.

Nevertheless, there still remains a need for a method for recovering substantially pure 2,4-DNT isomer from a dinitrotoluene process, especially without adversely affecting the isomer makeup of the commercially produced DNT product.

SUMMARY OF THE INVENTION

In its broadest aspect this invention relates to a method for recovering substantially pure 2,4-DNT isomer from its admixture with other DNT isomers. The process comprises contacting the mixture of DNT isomers with an aqueous sulfuric acid solution at an elevated temperature to form an aqueous sulfuric acid phase containing the DNT isomers, which acid phase is preferably substantially saturated with the DNT isomers. The aqueous acid phase is then cooled to precipitate substantially pure crystalline 2,4-DNT without precipitating significant amounts of other crystalline DNT isomers. Preferably the aqueous sulfuric acid solution is about 65–90 wt % sulfuric acid and the elevated temperature is between about 50° and 90° C.

It is preferred that the aqueous sulfuric acid solution be contacted with an amount of the DNT isomer mixture which yields an organic phase containing excess DNT isomers and an aqueous acid phase substantially saturated with DNT isomers. The aqueous acid phase is separated from the organic phase and cooled to effect precipitation of 2,4-DNT crystals, preferably at a temperature of about 40° C. or less. The temperature should not be so low that significant amounts of other DNT isomers precipitate or the aqueous sulfuric acid phase solidifies.

In another embodiment, substantially pure 2,4-DNT is recovered from a two-stage nitration process for producing dinitrotoluenes. The DNT process comprises:

(a) nitrating toluene in a first nitration stage with an aqueous mixture of sulfuric and nitric acids to form an organic phase containing mononitrotoluenes and a first aqueous spent acid phase, (b) separating the organic phase containing mononitrotoluenes from the first aqueous spent acid phase forming a first aqueous spent acid stream, (c) nitrating the mononitrotoluenes contained in the organic phase in a second nitration stage using a mixture of sulfuric and nitric acids to form an organic phase containing dinitrotoluenes and a second aqueous spent acid phase, (d) separating the organic phase containing dinitrotoluenes from the second aqueous spent acid phase forming a second aqueous spent acid stream, and (e) recovering dinitrotoluenes from the organic phase.

The first and second spent acid streams are advantageously conveyed to a nitration stage. Typically, the first spent acid stream is conveyed to the second nitration stage, preferably after reconcentration, and the second spent acid stream is cycled to the first nitration stage.

As applied to the DNT process the novel feature of this invention for recovering 2,4-DNT comprises:

(1) cooling at least a portion of the first or second aqueous spent acid streams to effect crystallization of 2,4-DNT, and (2) recovering the crystalline 2,4-DNT from the cooled spent acid stream.

Desirably, a further step would include:

(3) returning the portion of the aqueous spent acid stream to a nitration stage.

In yet another embodiment, substantially pure 2,4-DNT is recovered from a one-stage nitration process. This DNT process comprises:

(a) nitrating toluene in a nitration stage with an aqueous mixture of sulfuric and nitric acid to form a nitration reaction mixture comprising an organic phase containing dinitrotoluenes and an aqueous spent acid phase, (b) separating the organic phase from the aqueous spent acid phase forming an aqueous spent acid stream, and (c) recovering dinitrotoluenes from the organic phase.

The one-stage DNT process is typically operated as a loop reaction scheme in which the nitration reaction mixture is recycled to the nitration stage. A portion of the recycling nitration reaction mixture is continually withdrawn to a separation stage for separating the organic phase which contains the DNT product from the aqueous spent acid phase which may be returned to the loop reaction scheme in the form of an aqueous spent acid stream.

Again, the above steps (1) and (2), and optionally step (3), which compose the novel feature of this instant inventive process are applicable to the aqueous spent acid stream of the loop DNT reaction process.

The nitration reaction medium in a nitration stage, which comprises an organic phase containing nitrotoluenes and an aqueous acid phase, is normally at an elevated temperature due to the exothermic nature of a DNT process.

The method of this invention advantageously uses a portion of an existing aqueous spent acid stream of a DNT process. Such stream is saturated with DNT isomers having been in contact with the organic phase and thus the first step of a crystallization process is already completed.

The process of this invention provides a method by which substantially pure crystals of one specific DNT isomer are separated from a DNT reaction system. The inventive method provides substantially pure 2,4-DNT from a DNT process without having to separate this particular isomer from the DNT product mixture of up to six DNT isomers.

In addition to recovering 2,4-DNT of substantially high purity, several other advantages are realized:

Since the mononitration step of the two-stage DNT process is an exothermic reaction, the heat removal requirement is reduced because the temperature of the incoming, or recycled, spent acid stream is lowered.

Another advantage is the reduction of by-product formation in the recycled acid because of lower temperatures and reduced organic content in the aqueous phase. Such by-products include dinitrocresols, nitrous acid, TNT and other oxidative compounds.

Since the spent acid stream from which 2,4-DNT has been removed is now relatively more concentrated in the other DNT isomers, notably 2,6-DNT, it can serve as a source for further isomer separations.

As another advantage the separation of 2,4-DNT from a spent acid stream will reduce the burden of organic removal from this stream in subsequent processing, thereby freeing the equipment to process more material. Also, less organic material will be lost to the environment.

As yet another advantage, an inventory of 2,4-DNT can be accumulated and used to adjust off-specification product by either increasing the rate of removal of the 2,4-DNT isomer from a DNT process or by adding the isomer to the DNT product from the existing inventory. "Product specification," as it pertains to the mixture of DNT isomers produced by a DNT process as commercial product, refers to the allowable ranges for the 2,4-DNT/2,6-DNT ratio and the sum of 2,4-DNT plus 2,6-DNT in the product. Typically, for a commercial DNT product the 2,4-DNT/2,6-DNT ratio is about 80/20±1 and the sum of those two isomers is at least 95 wt %.

Further, by controlling the amount of substantially pure crystalline 2,4-DNT which is removed from the DNT process the DNT product can be maintained within the aimed-for specifications for commercial use.

DETAILED DESCRIPTION OF THE INVENTION

It has been found that substantially pure 2,4-DNT can be isolated from its admixture with the other DNT isomers by first intimately contacting, for example by agitation, the DNT isomer mixture with about 65 to 90 wt % aqueous sulfuric acid at a temperature from about 50° to 90° C. Such contacting should take place using a quantity of DNT isomer mixture in excess of that necessary for substantially saturating the aqueous acid phase with the DNT isomers and should continue for a time sufficient to effect such saturation. Needless to say, the DNT isomer mixture may first be dissolved in an aromatic hydrocarbon solvent, such as benzene, toluene, xylene and the like, which solution is contacted with the sulfuric acid phase. The aqueous sulfuric acid phase is separated from the organic phase of excess DNT materials and is cooled to a temperature of about 40° C. or less, preferably 25° C. or less, to effect crystallization of substantially pure 2,4-DNT, but not to a temperature which is sufficiently low to effect crystallization of a significant amount of another DNT isomer or to cause the aqueous sulfuric acid phase to freeze.

With respect to a DNT process it has also been found that by lowering the temperature of at least a portion of a spent acid stream which is saturated with a mixture of the DNT isomers a preferential crystallization of 2,4-DNT is effected.

Figure 1:
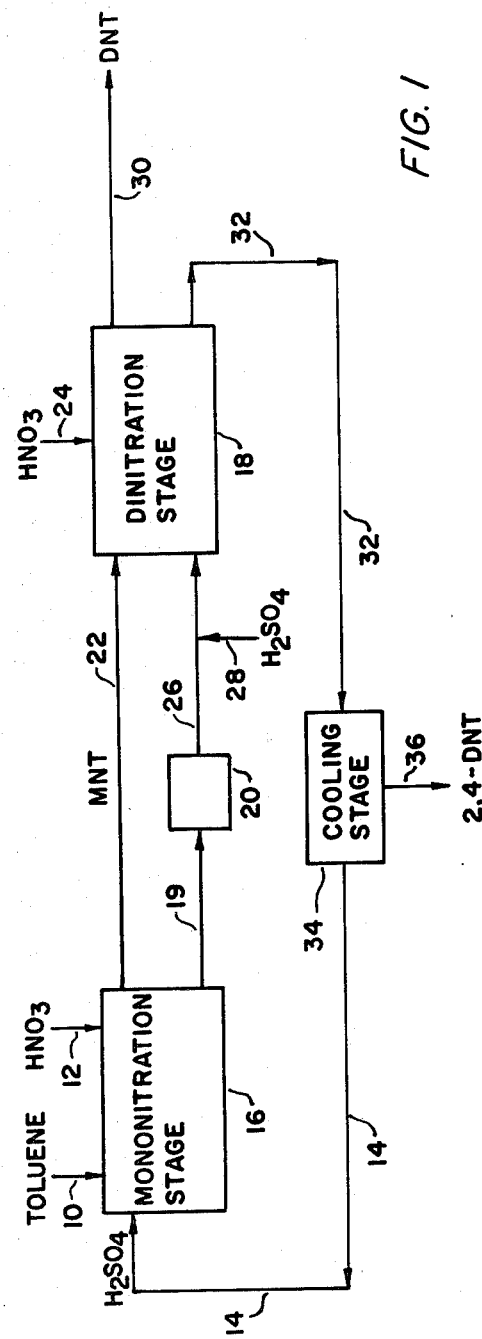
FIG. 1 is a schematic drawing depicting a two-stage dinitration process using the process of this invention.

Referring now to FIG. 1, toluene in line 10, nitric acid in line 12 and sulfuric acid in line 14 are fed into the mononitration stage 16 of the DNT process. The mononitration stage 16 may comprise a single reaction vessel or several reaction vessels connected in series. The reaction vessels are designed to provide for intimate contact between the two immiscible phases, the aqueous and the organic phases, by agitation. The sulfuric acid feed to this nitration stage is the spent acid generated in the second nitration stage 18 of the DNT process and is referred to as "cycle acid".

The aqueous spent acid stream 19 from the mononitration stage passes to reconcentrator 20 where it is reconcentrated for use as part of the mixed nitrating acid in the dinitration stage 18.

The organic phase containing the mononitrotoluenes produced in the first nitration stage is fed by line 22 into the second nitration stage 18 which also may comprise a single reaction vessel or a series of reaction vessels. Nitric acid from line 24, reconcentrated sulfuric acid from line 26, and optionally virgin sulfuric acid from line 28 are also added to the dinitration stage 18.

Product DNT leaves the dinitration stage 18 in line 30 for further purification in a typical purification stage, not shown.

The spent acid stream exits the dinitration stage 18 and passes in line 32 to cooling stage 34 where at least a portion of the spent acid stream is cooled to precipitate substantially pure 2,4-DNT which is removed by line 36. The cooled portion of the spent acid stream which had a substantial portion of its 2,4-DNT content removed and the remainder of the spent acid stream are cycled in line 14 back to the mononitration stage 16, being the primary source of sulfuric acid for the first nitration stage.

Figure 2:
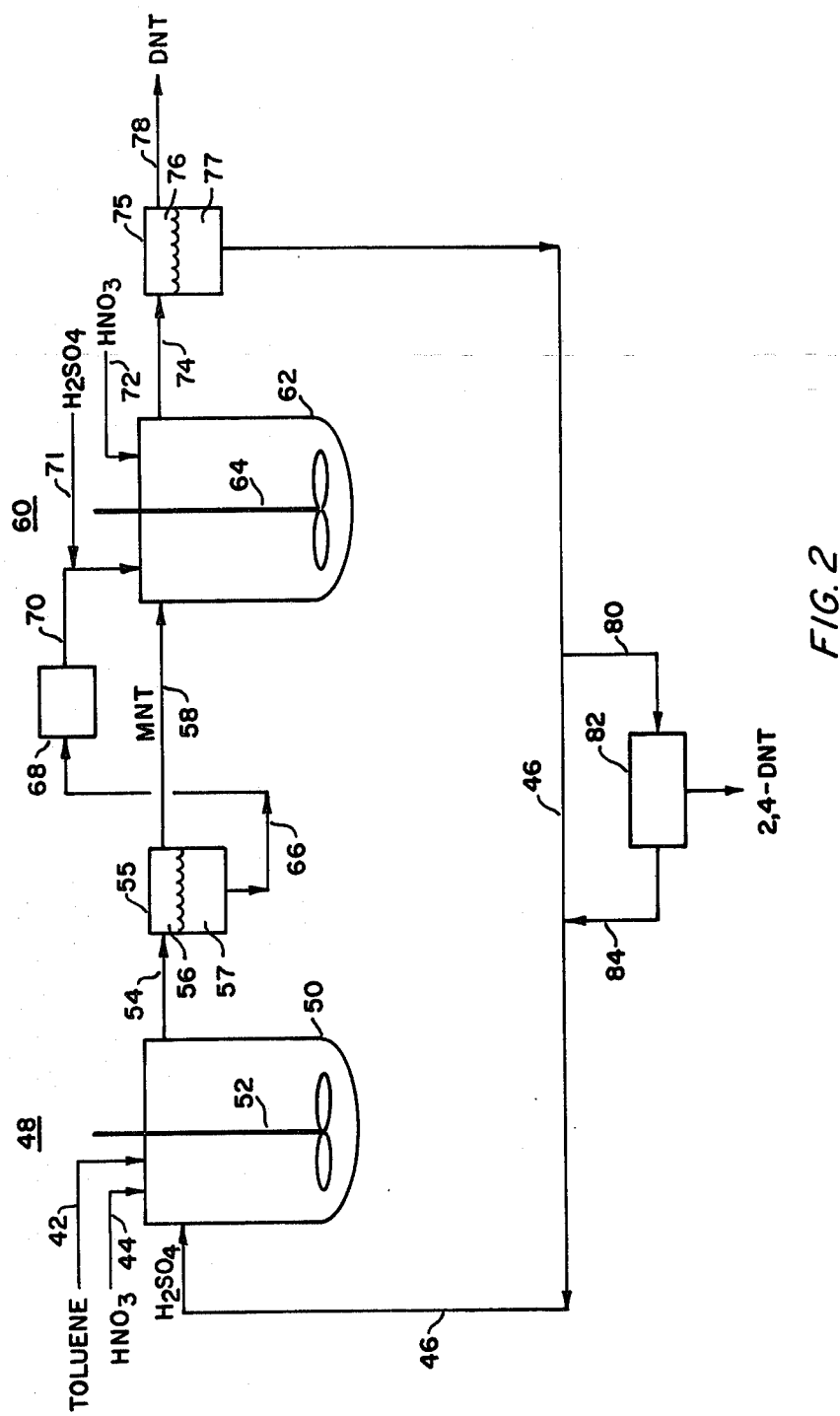
FIG. 2 depicts the arrangement of apparatus used in the preferred embodiment of FIG. 1.

Referring now to FIG. 2 which depicts a preferred embodiment for practicing the process for this invention, toluene at about 140 l/min in line 42; 60 to 90% aqueous nitric acid at about 90 l/min in line 44; and 80 to 90% aqueous sulfuric acid as cycle acid at about 300 l/min in line 46 are concurrently fed to the mononitration stage 48 which is depicted as comprising a single reaction vessel 50 having an agitator 52. It is preferred, however, that the mononitration zone 48 comprise about four such reaction vessels connected in series with the overflow rate passing from one reaction vessel to the next being approximately equal to the total flow rate of toluene, nitric acid and sulfuric acid fed into the first reaction vessel. The mononitration reaction medium which is maintained in the mononitration reaction stage 48 at a temperature from about 40° to 70° C., preferably about 50° C., exits via line 54 and passes into separator 55 in which the organic phase 56 and the spent aqueous acid phase 57 which compose the mononitration reaction medium are gravity separated.

The organic phase 56 which contains about 0.5 wt % unreacted toluene, 20 wt % DNT and 80 wt % mononitrotoluenes passes through line 58 at about 190 l/min into dinitration stage 60 which may comprise a single reaction vessel 62 equipped with agitator 64, but preferably comprises four such reaction vessels connected in series.

The spent acid from separator 55 in line 66, which is about 65 to 80 wt % sulfuric acid and about 0.1 to 1.0 wt % nitrous and nitric acids, is passed at about 350 l/min to reconcentrator 68 where the spent acid stream is heated to drive off water. A reconcentrated (90–98 wt %) sulfuric acid stream passes through line 70 at about 235 l/min into dinitration stage 60 along with 60 to 90% aqueous nitric acid from line 72 at about 100 l/min. Virgin sulfuric acid (90 to 98%) may be added by line 71, if necessary, or instead of the reconcentrated acid from reconcentrator 68.

The dinitration reaction medium, which is at a temperature from about 60° to 90° C., preferably about 70° C., and comprises DNT isomer product and spent nitrating acid, passes from reaction vessel 62 via line 74 at about 820 l/min into separator 75 where the DNT containing organic phase 76 and the spent aqueous acid phase 77 are separated. The organic phase 76 which contains about 99.8 wt % DNT product passes in line 78 to a washing and product recovery stage, not shown. The DNT product is washed typically in a series of agitated vessels to remove excess aqueous acid phase and also to remove impurities and by-products generated in the DNT process.

The spent aqueous acid phase 77 of about 70 to 90 wt % sulfuric acid from separator 75 is conveyed at about 300 l/min by line 46 as "cycle acid" to the mononitration stage 48. The cycle acid stream at this point is saturated with DNT isomers due to its previous intimate contact with the DNT product organic phase. The organic content of the spent acid phase 77 is between about 3 and 7 wt % of which about 78 to 84% is the 2,4-DNT isomer.

At least a portion, for example about 75 l/min, of the spent aqueous nitrating acid stream in line 46 is bled by line 80 into cooling zone 82 where the temperature of the bleed stream is lowered to less than about 40° C., preferably about 25° C. or less, to effect crystallization and separation of the 2,4-DNT isomer from the other DNT isomers in the cycle acid stream. Cooling zone 82 may comprise a long residence holding tank which would allow the spent aqueous acid phase to accumulate and to cool slowly by releasing its heat content to the ambient air. Preferably, the holding tank is cooled by external means so that the tank may be of smaller size. In addition, the holding tank can be operated as a batch or continuous operation and, in either case, the cooled portion of the spent aqueous acid stream is returned by line 84 to line 46 for cycling back to the mononitration stage 48.

Crystals of 2,4-DNT are allowed to accumulate in the holding tank of cooling zone 82 to a predetermined amount. At such time the bleed stream to the tank is closed and the tank drained leaving behind the crystalline product. Advantageously, the 2,4-DNT crystals are washed with water. The water and crystal mixture is heated to the melting point of 2,4-DNT and the resultant liquid mixture of water and molten 2,4-DNT is drained out of the tank. A physical separation of the water and the molten 2,4-DNT is made either prior to draining from the holding tank or concurrently with such draining. The separated 2,4-DNT may be sent to storage or to a hydrogenation process for the production of 2,4-toluenediamine. At least a portion of the cycle acid stream is again diverted to cooling zone 82 to complete the operation cycle. Preferably, when the feed of the bleed stream to the cooling zone is discontinued in order to drain the holding tank and wash the crystalline product, a second tank would be in operation to receive the portion of the cycle acid stream in order to maintain a somewhat continuous process.

Of course, the entire cycle acid stream may be directed to cooling zone 82 where its temperature is lowered to effect crystallization of 2,4-DNT. However, cooling the entire cycle acid stream would lead to an inconsistent DNT product from the DNT process which is the main objective of such process. The cooling of the cycle acid stream and the physical separation of the crystalline product may be performed on a constantly flowing cycle acid stream.

In another embodiment of the invention for producing substantially pure 2,4-DNT isomer from a spent nitrating acid phase of a two-stage DNT process, the mononitration spent acid stream in line 66 from separator 55 is cooled to effect crystallization of the desired product. Since the cycle acid stream from the dinitration stage 60 contains a mixture of DNT isomers and is conveyed to mononitration stage 48, the nitration reaction medium in the mononitration stage 48 will also contain the DNT isomers. Accordingly, the spent aqueous acid phase 57 which will have been in equilibrium with the organic phase 56 will also contain the DNT isomer mixture. In this embodiment, not shown, it is desirable that reconcentrator 68 in which water is driven off from the spent acid phase also comprise a subsequent cooling zone holding tank similar to cooling zone 82 for the cycle acid stream. In this manner the spent nitrating acid stream 66 from the mononitration stage 48 is first reconcentrated and then cooled to effect crystallization of the 2,4-DNT isomer.

The separated spent acid phases from the separators 55 and 75 contain organic materials in the range of about 2 to 8 wt % depending on the sulfuric acid concentrations and temperatures. Spent acid stream 66 is nominally generated with a sulfuric acid strength between about 65 and 80 wt % at a temperature between about 35° and 70° C. Cycle acid stream in line 46 typically has a sulfuric acid strength between about 65 and 90 wt % at a temperature between about 50° and 90° C. Of the total organic compounds dissolved in the spent acid streams between about 70 and 90 wt % is 2,4-DNT.

Substantially pure 2,4-DNT can be removed from a continuous two-stage DNT process as depicted by FIG. 2 without adversely affecting the specification on the final DNT product. For example, a production rate of $470 \times 10^6$ lb-DNT/year is assumed for the DNT process from which 2,4-DNT will be continually removed. The guidelines within which the DNT process must work are the following product DNT specifications: 2,4-DNT 79–81% and 2,6-DNT 19–21% (normalized); and purity (2,4-DNT+2,6-DNT) 94.80 wt % minimum. Operating under such conditions for a one year continuous operation, 2,4-DNT can safely be removed from the DNT process at a rate of $4 \times 10^6$ lb/year without having the final DNT product isomer mixture going out of specification.

Figure 3:
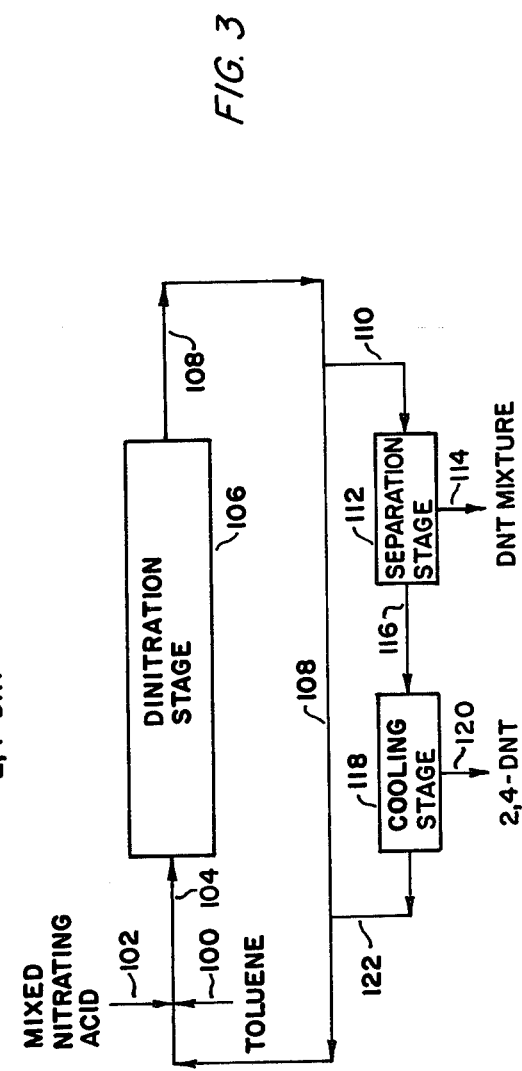
FIG. 3 is a schematic drawing depicting a one-stage dinitration process incorporating the inventive process.

Referring to FIG. 3, which shows a cyclic one-stage DNT process, toluene in line 100 and aqueous nitrating acid comprising nitric and sulfuric acids in line 102 are fed into and maintained in a moving stream in conduit 104. A turbulent, intimate mixing of the organic and aqueous phases composing the reaction medium is sustained in moving stream 104 as it passes in conduit 104 through dinitration stage 106 where the reaction medium is maintained at a temperature between about 70° and 90° C. for a time sufficient to produce a nitration reaction product stream in line 108 comprising DNT and aqueous spent acid phase. The reaction product stream maintained at a temperature above 60° C. is cycled by line 108 to line 104 to receive fresh toluene and nitrating acid before entering the dinitration stage 106.

At least a portion of the nitration reaction product stream is withdrawn from the loop reaction system by line 110 for the separation of the DNT containing organic phase from the aqueous spent acid phase in separation stage 112 maintained above 60° C. A physical separation step in separation stage 112 permits the liquid DNT product phase to pass by line 114 to a purification stage, not shown, where the DNT isomer mixture is washed and purified. An aqueous spent acid stream passes from separation stage 112 by line 116 to cooling stage 118 where the stream is cooled to a temperature less than about 40° C., preferably less than about 25° C., to effect crystallization of substantially pure 2,4-DNT which is removed by line 120. The cooled aqueous spent acid stream is conducted by line 122 back to recycle line 108 containing the remaining portion of the nitration reaction product stream.

A more detailed description of a one-stage loop reaction scheme for making DNT from toluene is presented in U.S. Pat. No. 3,178,481 which is incorporated by reference.

The following examples are provided to illustrate the invention and are not intended to restrict the scope of the invention:

EXAMPLE I

A cycle acid was prepared by continually nitrating a combination of reagent grade mononitrotoluene (MNT) isomer mixture (60.2 wt % o-MNT; 4.2 wt % m-MNT; 35.6 wt % p-MNT) to DNT with a dinitrating mixture of acids (44.8 mole % sulfuric acid; 17.4 mole % nitric acid; 37.8 mole % water) at 70.5±0.7° C. and a residence time of 10.9 minutes. Steady state spent acid concentration (cycle acid), analyzed by ion chromatography, was 82.3 wt % sulfuric acid and 2.7 wt % nitric acid on an organic free basis. Table I shows a gas chromatographic analysis of the organic product which indicated a 91.6% conversion to DNT. The product was a typical DNT isomer distribution (2,4-DNT/2,6-DNT=79/21; purity 95.6%, both on MNT free basis).

TABLE I

| ISOMERS | ORGANIC PRODUCT wt % | ISOLATED CRYSTALS FROM CYCLE ACID wt % |
|---|---|---|
| o-MNT | 2.89 | trace |
| m-MNT | 0.46 | trace |
| p-MNT | 3.08 | 0 |
| 2,6-DNT | 18.84 | 1.53 |
| 2,5-DNT | 0.57 | 0.04 |
| 2,4-DNT | 70.54 | 98.35 |
| 3,5-DNT | 0 | 0 |
| 2,3-DNT | 1.46 | 0 |
| 3,4-DNT | 2.16 | 0.07 |
| TNT | 0 | 0 |
|  | 100.00 | 99.99 |

After separating the organic and aqueous phases, approximately 4 liters of the cycle acid were collected in a large glass vessel and allowed to cool from 70° C. to approximately 25° C. Fibrous crystals were separated from the mixture. Between 60 and 70% of the dissolved 2,4-DNT was removed, i.e. about 130 g out of 190 g. The crystals were analyzed by gas chromatography and revealed an isomer distribution as shown in Table I. This example shows substantially pure crystals of 2,4-DNT (98.4%) were isolated.

EXAMPLE II

Two batch tests were conducted in which a mixture of DNT isomers was contacted with 82 wt % aqueous sulfuric acid solution at about 70° C. for one hour, long enough to saturate the aqueous acid solutions with the organic materials. The excess DNT was then separated. One aqueous sample was placed in a 40° C. bath, while the other was allowed to cool to room temperature (25° C.). Table II shows the isomer make-up of the starting DNT mixture, the DNT isomer distribution in the 82% sulfuric acid at 70° C., and the gas chromatographic analysis of the crystals isolated at 40° C. and at 25° C. from the two batch solutions. As can be seen from Table II, crystals grown in both batches of the acid solutions contained higher concentrations of 2,4-DNT than the starting DNT isomer mixture; namely, 88.2% and 95.3%, respectively, versus 65.9% 2,4-DNT.

TABLE II

| ISOMER | STARTING DNT wt % | DNT in 82% H$_2$SO$_4$ at 70° C. wt % | DNT in 82% H$_2$SO$_4$ at 70° C. normalized wt % | CRYSTALS of 2,4-DNT at 40° C. wt % | CRYSTALS of 2,4-DNT at 25° C. wt % |
|---|---|---|---|---|---|
| o-MNT | trace | trace | trace | 0 | 0 |
| m-MNT | trace | trace | 0.01 | trace | trace |
| p-MNT | 0 | 0 | 0 | 0 | 0 |
| 2,6-DNT | 30.02 | 0.60 | 19.27 | 10.19 | 4.33 |
| 2,5-DNT | 0.50 | 0.01 | 0.40 | 0.19 | 0.08 |
| 2,4-DNT | 65.94 | 2.44 | 78.33 | 88.23 | 95.30 |
| 3,5-DNT | 0 | 0 | 0 | 0 | 0 |
| 2,3-DNT | 1.37 | 0.02 | 0.74 | 0.58 | 0.20 |
| 3,4-DNT | 2.14 | 0.04 | 1.26 | 0.81 | 0.09 |
| TNT | 0.02 | 0 | 0 | 0 | 0 |
| | 99.99 | 3.11 | 100.01 | 100.00 | 100.00 |

EXAMPLE III

In a two stage nitration process substantially as depicted in FIG. 2, a storage tank was situated in line 66 between the separator 55 and reconcentrator 68 to serve as storage for spent acid from the mononitration stage 48. The temperature of the spent acid phase into the tank was between 60° and 70° C. The composition was 70 to 75 wt % sulfuric acid and 0.1 to 1.0 wt % nitric acid. The contents of the tank was cooled to about 25° C. The crystalline material which was isolated had a 2,4-DNT content of about 97.0 wt % as shown in Table III.

TABLE III

Analysis of Crystalline Material: (Normalized)

| o-MNT | Trace |
|---|---|
| m-MNT | 0.18% |
| p-MNT | 0 |
| 2,6-DNT | 2.24 |
| 2,5-DNT | 0.04 |
| 2,4-DNT | 96.95 |
| 2,3-DNT | 0.16 |
| 3,4-DNT | 0.43 |
| TNT | 0 |
| | 100.00 |

STATEMENT OF INDUSTRIAL APPLICATION

The invention provides a method for obtaining substantially pure 2,4-DNT from a DNT process. 2,4-DNT is the raw material for 2,4-toluenediamine, a chemical intermediate used in manufacturing specialty toluene diisocyanate and dye stuffs.

I claim:

1. A method for preparing substantially pure 2,4-dinitrotoluene from its admixture with other dinitrotoluene isomers which comprises:
   (a) contacting an organic phase comprising the mixture of dinitrotoluene isomers with aqueous sulfuric acid at an elevated temperature for a time sufficient to form an aqueous sulfuric acid phase containing the dinitrotoluene isomers;
   (b) cooling the aqueous sulfuric acid phase to effect precipitation of substantially pure 2,4-dinitrotoluene crystals without precipitation of a significant amount of another dinitrotoluene isomer; and
   (c) collecting the crystals of 2,4-dinitrotoluene.

2. The method of claim 1 in which the contacting step yields an organic phase containing excess dinitrotoluene isomers and an aqueous acid phase substantially saturated with dinitrotoluene isomers and the aqueous acid phase is separated from the organic phase.

3. The method of claim 2 in which the aqueous sulfuric acid phase is from about 65 to 90 wt % sulfuric acid.

4. The method of claim 2 in which the DNT isomer mixture and the aqueous sulfuric acid phase is contacted at a temperature between about 50° and 90° C.

5. The method of claims 2, 3 or 4 in which the sulfuric acid phase is cooled to a temperature less than about 40° C.

6. The method of claim 5 in which the sulfuric acid phase is cooled to a temperature less than about 25° C.

7. The method of claims 2, 3 or 4 in which the dinitrotoluene isomer mixture is first dissolved in an aromatic hydrocarbon solvent.

8. In a method for producing dinitrotoluenes which comprises:
   (a) nitrating toluene in a first nitration stage with an aqueous mixture of sulfuric and nitric acids to form an organic phase containing mononitrotoluenes and a first aqueous spent acid phase;
   (b) separating the organic phase from the first aqueous spent acid phase forming a first aqueous spent acid stream;
   (c) nitrating the mononitrotoluenes contained in the organic phase in a second nitration stage using a mixture of sulfuric and nitric acids to form an organic phase containing dinitrotoluenes and a second aqueous spent acid phase;
   (d) separating the organic phase from the second aqueous spent acid phase forming a second aqueous spent acid stream; and
   (e) recovering dinitrotoluenes from the organic phase;
the method comprising
   (f) cooling at least a portion of the first or second aqueous spent acid stream to effect crystallization of 2,4-dinitrotoluene; and
   (g) recovering the 2,4-dinitrotoluene crystals from the cooled aqueous spent acid stream.

9. The method of claim 8 which includes the following step:
   (h) returning the cooled portion of the aqueous spent acid stream to a nitration stage.

10. The method of claims 8 or 9 in which the portion of the first or the second aqueous spent acid stream is cooled to a temperature less than about 40° C.

11. The method of claim 10 in which the portion of the first or the second aqueous spent acid stream is cooled to a temperature less than about 25° C.

12. The method of claims 8 or 9 wherein a portion of the aqueous spent acid stream from the second nitration stage is cooled.

13. The method of claims 8 or 9 wherein a portion of the aqueous spent acid stream from the first nitration stage is cooled.

14. The method of claim 12 in which the portion of the spent acid stream is cooled to a temperature less than about 40° C.

15. The method of claim 12 in which the portion of the spent acid stream is cooled to a temperature less than about 25° C.

16. In a method for producing dinitrotoluenes which comprises:
   (a) nitrating toluene in a nitration stage with an aqueous mixture of sulfuric and nitric acids to form a nitration reaction mixture comprising an organic phase containing dinitrotoluenes and an aqueous spent acid phase;

(b) separating the organic phase from the aqueous spent acid phase forming an aqueous spent acid stream; and (c) recovering dinitrotoluenes from the organic phase; the method comprising (d) cooling at least a portion of the aqueous spent acid stream to effect crystallization of 2,4-dinitrotoluene; and (e) recovering the 2,4-dinitrotoluene crystals from the cooled aqueous spent acid stream.

17. The method of claim 16 in which at least a portion of the nitration reaction mixture is separated into an organic phase and an aqueous spent acid stream with the remaining portion of the nitration reaction mixture recycled to the nitration stage.

18. The method of claim 17 which includes the following step:

(f) returning the cooled portion of the aqueous spent acid stream to the nitration stage.

19. The method of claims 16, 17 or 18 in which the portion of the spent acid stream is cooled to a temperature less than about 40° C.

20. The method of claim 19 in which the portion of the spent acid stream is cooled to a temperature less than about 25° C.

* * * * *